(12) United States Patent
Budri et al.

(10) Patent No.: US 7,038,222 B1
(45) Date of Patent: May 2, 2006

(54) SYSTEM AND METHOD FOR USING AREAS NEAR PHOTO GLOBAL ALIGNMENT MARKS OR UNPATTERNED AREAS OF A SEMICONDUCTOR WAFER TO CREATE STRUCTURES FOR SIMS OR E-BEAM OR XRD TESTING

(75) Inventors: Thanas Budri, Portland, ME (US); Aaron Michael Smith, Harpswell, ME (US); Neil Suresh Patel, Portland, ME (US); Loren Charles Krott, Gorham, ME (US)

(73) Assignee: National Semiconductor Corporation, Santa Clara, CA (US)

( * ) Notice: Subject to any disclaimer, the term of this patent is extended or adjusted under 35 U.S.C. 154(b) by 110 days.

(21) Appl. No.: 10/869,681

(22) Filed: Jun. 16, 2004

(51) Int. Cl.
*H01L 21/66* (2006.01)
*G01R 31/26* (2006.01)

(52) U.S. Cl. ................. 250/492.2; 250/492.3; 250/306; 250/307; 250/309; 250/310; 700/121; 257/E21.001

(58) Field of Classification Search ................. None
See application file for complete search history.

(56) References Cited

U.S. PATENT DOCUMENTS 5,625,288 A * 4/1997 Snyder et al. ........... 324/158.1

* cited by examiner

*Primary Examiner*—Nikita Wells

(57) ABSTRACT

A system and method is described for using areas in or near photo global alignment marks or in or near unpatterned areas of a semiconductor wafer to create structures for secondary ion mass spectroscopy (SIMS) testing or electron beam (E-Beam) testing or X-ray diffraction (XRD) testing of the semiconductor wafer. The present invention makes it possible to obtain wafer level information about the front-end processing of the semiconductor wafers. The SIMS/E-Beam/XRD testing measures characteristics such as the dopant content, thickness variations, and defect density of the wafers. The present invention eliminates the need to build individual test structures within product dies and eliminates the need to build scribe line structures near the product dies.

20 Claims, 5 Drawing Sheets

SYSTEM AND METHOD FOR USING AREAS NEAR PHOTO GLOBAL ALIGNMENT MARKS OR UNPATTERNED AREAS OF A SEMICONDUCTOR WAFER TO CREATE STRUCTURES FOR SIMS OR E-BEAM OR XRD TESTING

TECHNICAL FIELD OF THE INVENTION

The present invention is generally directed to manufacturing technology for semiconductor wafers and, in particular, to a system and method for using areas near photo global alignment marks or unpatterned areas of a semiconductor wafer to create test structures for SIMS testing or E-Beam testing or X-ray diffraction testing of the semiconductor wafer.

BACKGROUND OF THE INVENTION

The size of semiconductor devices continues to shrink as advances are made in semiconductor manufacturing technology. In particular, transistor junction depths continue to become shallower. Secondary ion mass spectroscopy (SIMS) and electron beam (E-Beam) shallow probe analysis and X-Ray Diffraction (XRD) are prior art techniques for testing semiconductor wafers. The size of test structures on a semiconductor wafer that are used as locations for conducting such tests also continues to shrink.

Prior art test structures located at the scribe lines of a semiconductor wafer are unable to provide adequate areas to perform (1) the SIMS test and analysis or (2) the E-Beam test and analysis or (3) the X-Ray diffraction test and analysis with the accuracy and precision required by these processes. That is, the prior art test structures located at the scribe lines can not provide an adequate area to properly perform the SIMS/E-Beam/XRD tests on a semiconductor wafer.

Because junction depths are becoming shallower, the primary ion and electron beam energies of SIMS and of E-Beam probes must be correspondingly lower. This causes the SIMS and E-beam probes to have higher levels of beam aberration. These lower ion and electron beam energies and higher levels of beam aberration require a test area that is at least one hundred microns square. The required test area is at least one hundred microns (100 µm) by one hundred microns (100 µm). A micron is one millionth of a meter (1 µm=$10^{-6}$ m).

The SIMS test is a destructive technique. Any attempt to use it for scribe line structures near product wafer areas (or on individual test structures created within a die) can be costly. In addition, it is necessary to provide protective masks. The risk of contamination is also present.

Although claimed to be non-destructive, the E-Beam test and the XRD test cannot reasonably be used for testing near product wafer areas because it is possible that charges may build up while the electron beam or the X-ray beam is in operation. The accumulated charges may be very damaging to the nearby circuitry of the integrated circuit die.

Therefore, there is a need in the art for a system and method for identifying and using other types of areas in a semiconductor wafer to create structures for the testing and analysis of the semiconductor wafer using either a SIMS test and analysis, an E-Beam test and analysis, or an X-ray diffraction test and analysis.

SUMMARY OF THE INVENTION

To address the above-discussed deficiencies of the prior art, it is a primary object of the present invention to provide a system and method for using areas in or near photo global alignment marks or in or near unpatterned areas of a semiconductor wafer to create test structures for SIMS testing or E-Beam testing or XRD testing of the semiconductor wafer.

In one advantageous embodiment of the method of the invention a test structure is created within non-yield area of a semiconductor wafer (e.g., a photo global alignment mark). Then the test structure is opened and the semiconductor wafer is processed using standard fabrication processes. Then either a secondary ion mass spectroscopy (SIMS) test or an electron beam (E-Beam) test or an X-ray diffraction (XRD) test is performed on the test structure. If the tested semiconductor wafer fails to meet specified quality control standards, then other semiconductor wafers in the same semiconductor wafer lot will not be processed until the defects in the wafers have been corrected.

The present invention makes it possible to obtain wafer level information about the front-end processing of semiconductor wafers. The SIMS/E-Beam/XRD testing measures characteristics such as dopant content, thickness variations, and defect density of the wafers. The present invention eliminates the need to build individual test structures within product dies and eliminates the need to build scribe line structures near the product dies.

It is an object of the present invention to provide a system and method for testing semiconductor wafers.

It is also an object of the present invention to provide a system and method for obtaining wafer level information about the front-end processing of semiconductor wafers.

It is yet another object of the present invention to provide a system and method for manufacturing test structures in non-yield areas of a semiconductor wafer.

It is still another object of the present invention to provide a system and method for using areas in or near photo global alignment marks or in or near unpatterned areas of a semiconductor wafer to create test structures for SIMS testing or E-Beam testing or XRD testing of the semiconductor wafer.

The foregoing has outlined rather broadly the features and technical advantages of the present invention so that those skilled in the art may better understand the detailed description of the invention that follows. Additional features and advantages of the invention will be described hereinafter that form the subject of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior uses, as well as future uses, of such defined words and phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

Figure 1:
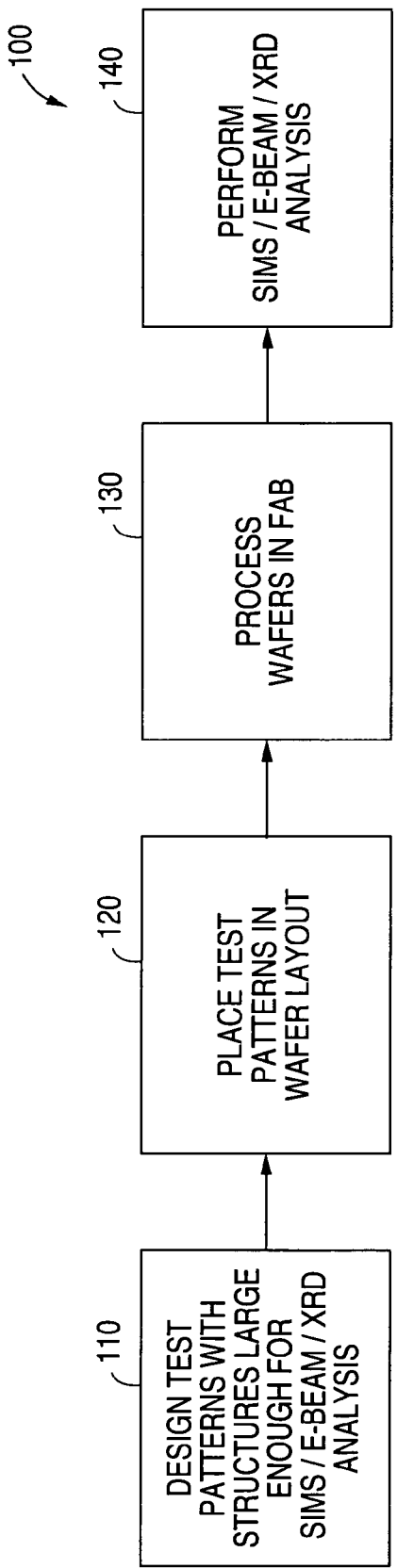
FIG. 1 illustrates a prior art method for providing test patterns on a semiconductor wafer on which to perform a SIMS test and analysis or an E-Beam test and analysis or an XRD test and analysis.

FIGS. 1 through 8, discussed below, and the various embodiments used to describe the principles of the present invention in this patent document are by way of illustration only and should not be construed in any way to limit the scope of the invention. Those skilled in the art will understand that the principles of the present invention may be implemented in any type of suitably arranged integrated circuit.

To simplify the drawings the reference numerals from previous drawings may sometimes not be repeated for structures that have already been identified.

FIG. 1 illustrates a prior art method for providing test patterns on a semiconductor wafer on which to perform a SIMS test and analysis or an E-Beam test and analysis or an XRD test and analysis. In the first step of the prior art method test patterns are designed that have structures that are large enough to accommodate subsequent SIMS/E-Beam/XRD analysis (step 110). The test patterns are typically located at the scribe lines. The test patterns occupy space in the product wafer area, either on the mask or embedded in the semiconductor die.

The test patterns are then placed in the semiconductor wafer layout (step 120). The test patterns consume area on the wafer that could otherwise be used as product wafer area. If the test patterns are embedded in a semiconductor die, then the die size must be increased. An increased die size reduces the number of dies that may be placed on a given semiconductor wafer. The semiconductor wafers are then processed using standard fabrication processes (step 130). Then the SIMS/E-Beam/XRD analysis is performed on the test patterns (step 140).

The size of semiconductor devices continues to shrink as advances are made in semiconductor manufacturing technology. This means that the size of the scribe lines on the semiconductor wafers also continues to shrink. For this reason the prior art test structures located at the scribe lines can not provide an adequate area to perform the SIMS/E-Beam/XRD test and analysis with the required accuracy and precision. Because junction depths are becoming shallower, the primary ion and electron beam energies of SIMS and of E-Beam probes must be correspondingly lower. This causes the SIMS and E-beam probes to have higher levels of beam aberration. These lower ion and electron beam energies and higher levels of beam aberration require a test area that is at least one hundred microns square. The required analysis area is at least one hundred microns (100 μm) by one hundred microns (100 μm). A micron is one millionth of a meter (1 μm=$10^{-6}$ m).

Figure 2:
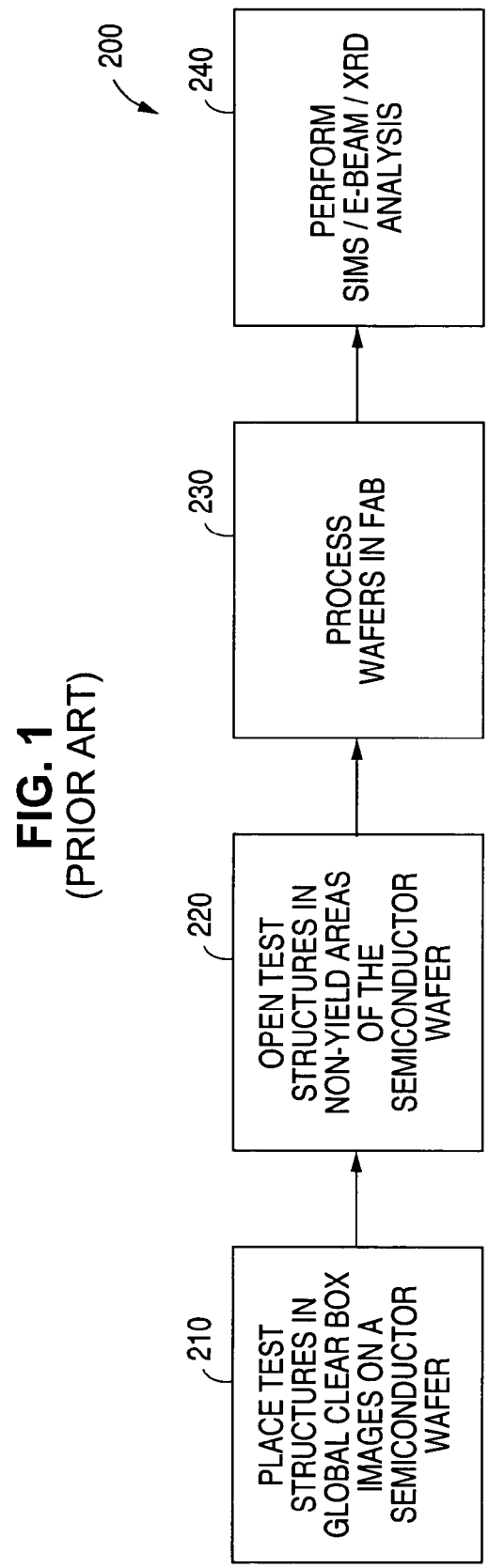
FIG. 2 illustrates an advantageous embodiment of a method of the present invention for providing test structures on non-yield areas of a semiconductor wafer on which to perform a SIMS test and analysis or an E-Beam test and analysis or an XRD test and analysis.

FIG. 2 illustrates an advantageous embodiment of a method of the present invention for providing test structures on non-yield areas of a semiconductor wafer on which to perform a SIMS test and analysis or an E-Beam test and analysis or an XRD test and analysis. In the first step of the method test structures are placed in standard global clear box images of the semiconductor wafer (step 210). The test structures are used instead of prior art test patterns. The global clear box images are capable of accommodating a subsequent SIMS/E-Beam/XRD test and analysis. The test structures are then opened in non-yield areas of the semiconductor wafer (step 220). The non-yield areas are non-yield areas because of the patterning around the global alignment marks. The semiconductor wafers are then processed using standard fabrication processes (step 230). Then a SIMS/E-Beam/XRD test and analysis is performed in the test structures in the non-yield areas (step 240).

Figure 3:
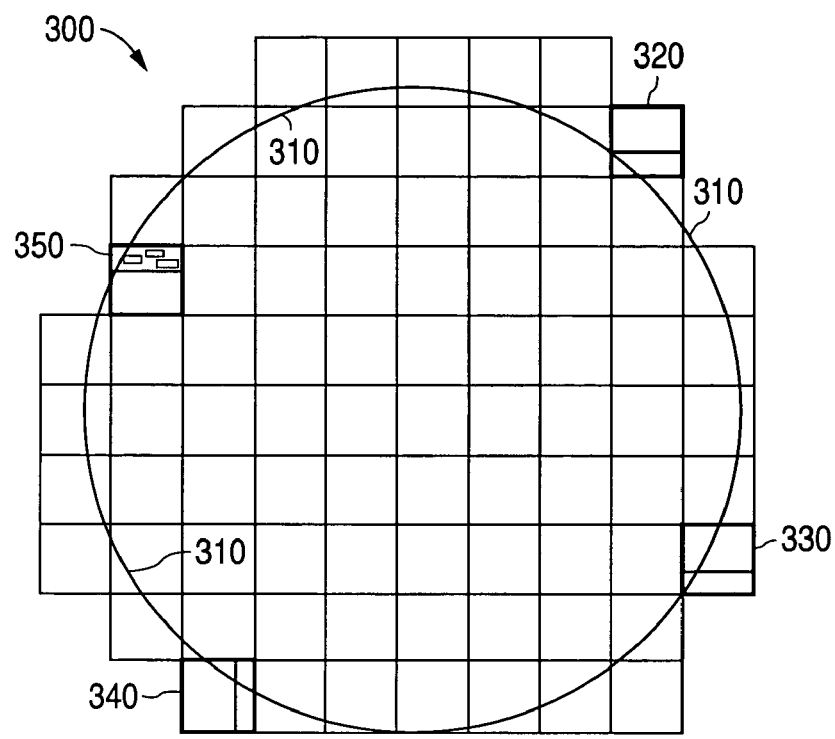
FIG. 3 illustrates a plan view of an exemplary semiconductor wafer map showing the location of four global alignment marks near the circumference of the wafer.

To better understand the system and method of the present invention, consider the plan view of an exemplary semiconductor wafer map 300 shown in FIG. 3. The circumference of the circular wafer is designated with reference numeral 310. In the wafer map 300 there are four exemplary global alignment marks, 320, 330, 340 and 350, located near the circumference 310 of the wafer.

Figure 4:
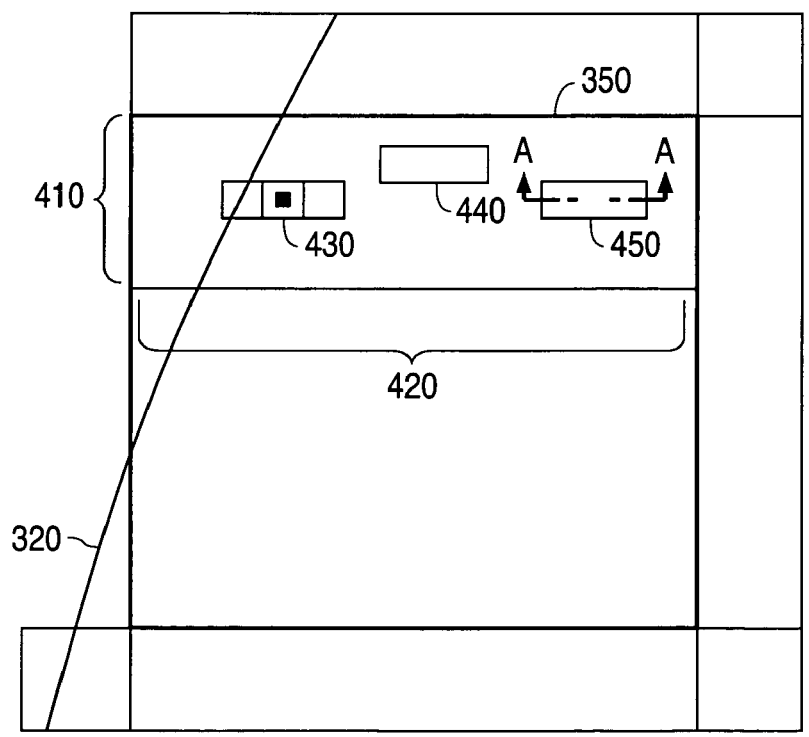
FIG. 4 illustrates an enlarged view of one of the four global alignment marks shown in FIG. 3 showing the placement of three exemplary test areas in an unpatterned region of the global alignment mark.

FIG. 4 illustrates an enlarged view of global alignment mark 350 shown in FIG. 3. A portion of the global alignment mark 350 is unpatterned. In the embodiment shown in FIG. 4 the unpatterned portion is a rectangle having a width 410 and a length 420. Three exemplary SIMS test areas 430, 440 and 450 are placed in the unpatterned region of global alignment mark 350.

It is understood that the use of the unpatterned region of global alignment mark 350 is merely one example and that the present invention is not limited to use in or near global alignment marks. It is clear that it is also possible to use unpatterned regions of the semiconductor wafer that are not located in or near a global alignment mark.

Figure 5:
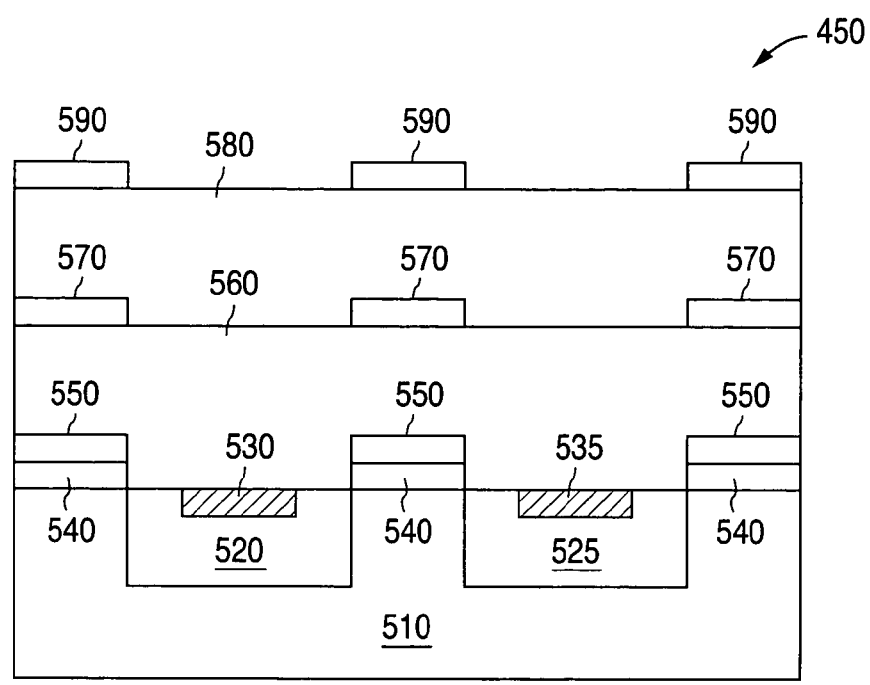
FIG. 5 illustrates a cross sectional view of one of the test areas shown in FIG. 4 taken along the line A—A.

FIG. 5 illustrates a cross sectional view of the SIMS test area 450 shown in FIG. 4 taken along the line A—A. FIG. 5 illustrates the underlying structures of the wafer that may be subjected to a SIMS analysis. Although the test area is referred to as a SIMS test area, it is understood that the SIMS test area may also be subjected to an E-Beam test and analysis or subjected to an XRD test and analysis.

The underlying active substrate of the SIMS test area 450 is designated with reference numeral 510. The following description of the underlying structures in the SIMS test area 450 is merely an illustrative example. It is understood that other types of structures may underlie a SIMS test area. The semiconductor manufacturing techniques needed to create the underlying structures (e.g., mask and etch processes) are well known and will not be described.

Two N-Well structures (520, 525) are formed within the underlying active substrate 510. A P type lightly doped drain (PLDD)/P type Halo layer 530 is formed within N-Well structure 520. The term Halo refers to a physical region that is located immediately under the LDD implant. Similarly, a P type (P+) layer 535 is formed within N-Well structure 525.

A portion of active substrate 510 that is located between N-well structure 520 and N-well structure 525 is covered with a layer of gate oxide/poly 540. In addition, portions of active substrate 510 located at the outer end of N-well structure 520 and the outer end of N-well structure 525 are covered with a layer of gate oxide/poly 540. The layers of gate oxide/poly 540 are covered with a layer of silicon oxynitride (SiON) 550.

Then a layer of dielectric material 560 is applied to cover the layers of silicon oxynitride (SiON) 550, and the N-well structure 520, and the P type lightly doped drain (PLDD)/P type Halo layer 530, and the N-well structure 525, and the P type (P+) layer 535. Portions of metal layer 570 are formed on dielectric layer 560. Then a layer of dielectric material 580 is applied over metal layer 570 and dielectric layer 560. Lastly, portions of metal layer 590 are formed on dielectric layer 580.

Exemplary SIMS test area 450 comprises a PLDD/Phalo portion shown on the left hand side of FIG. 5 and a P type (P+) portion shown on the right hand side of FIG. 5.

Figure 6:
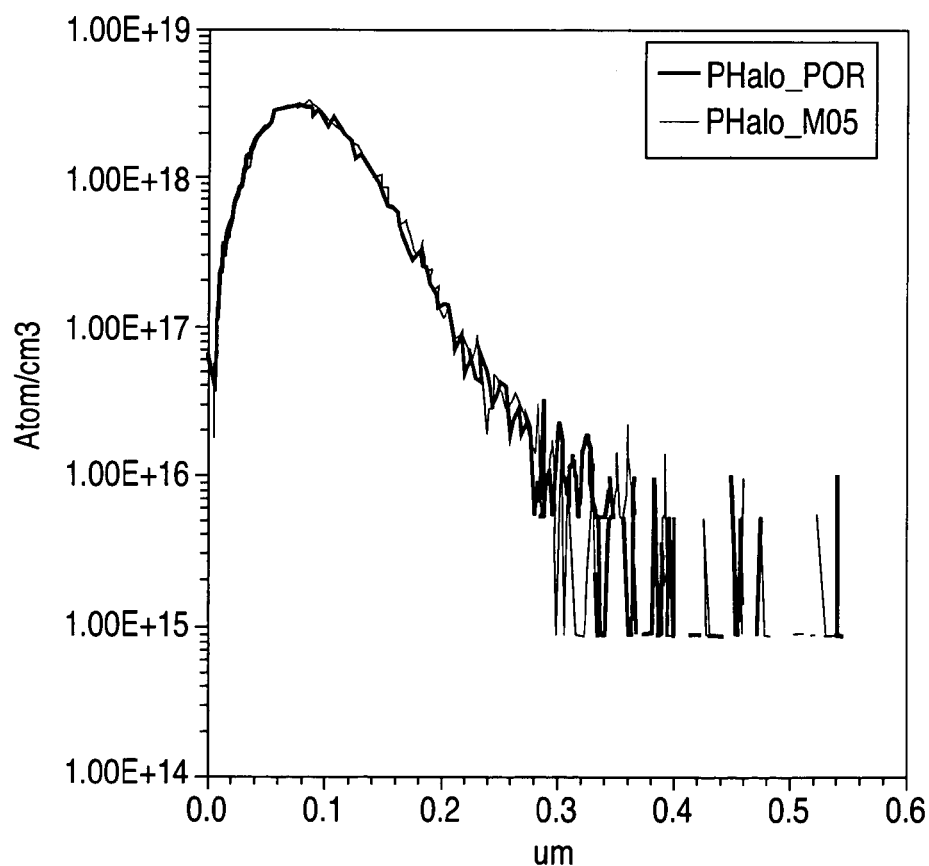
FIG. 6 illustrates a graph of the results of an exemplary SIMS test and analysis obtained from a PLDD/PHalo portion of the test area shown in FIG. 5.

FIG. 6 illustrates a graph of the results of an exemplary SIMS test and analysis obtained from the PLDD/PHalo portion of the SIMS test area 450.

Figure 7:
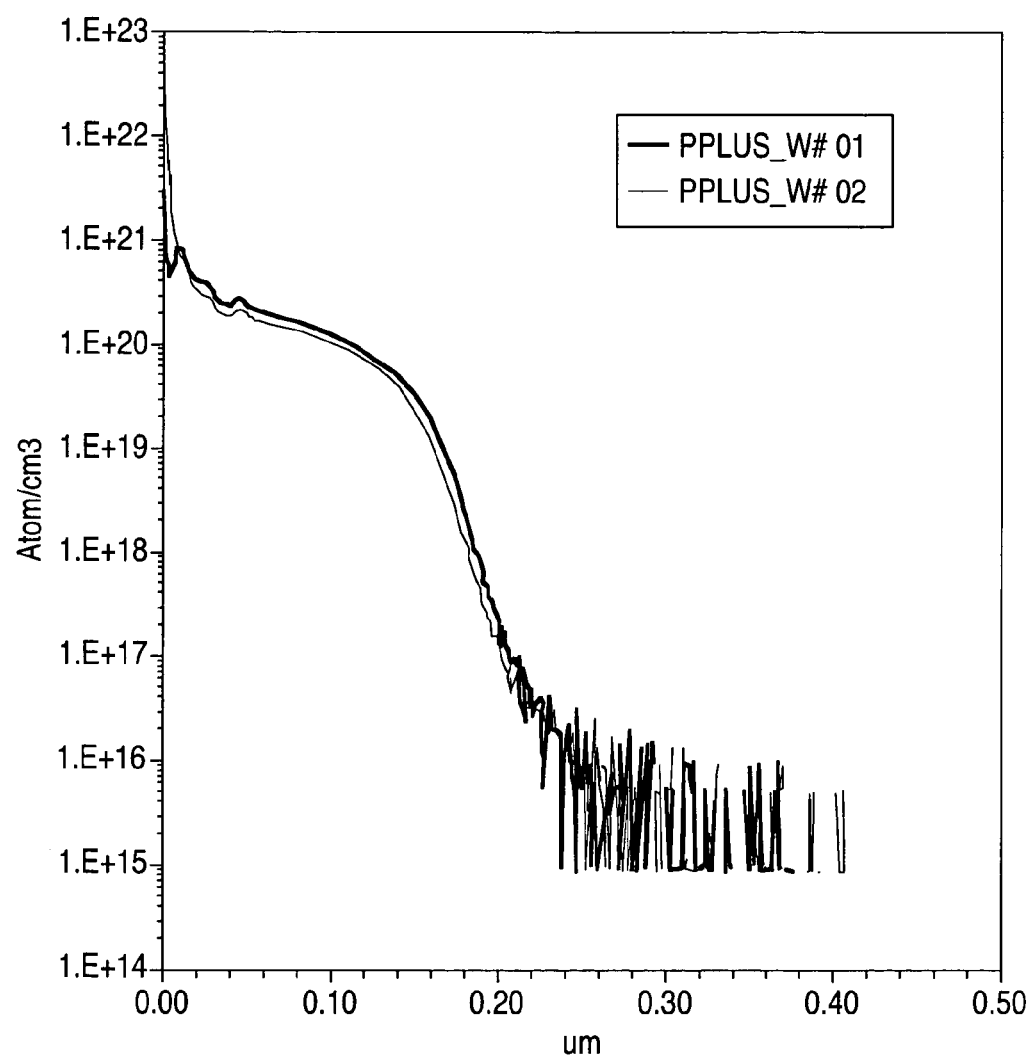
FIG. 7 illustrates a graph of the results of a SIMS exemplary SIMS test and analysis obtained from a P type (P+) portion of the test area shown in FIG. 5.

FIG. 7 illustrates a graph of the results of a SIMS exemplary SIMS test and analysis obtained from the P type (P+) portion of the SIMS test area 450.

Figure 8:
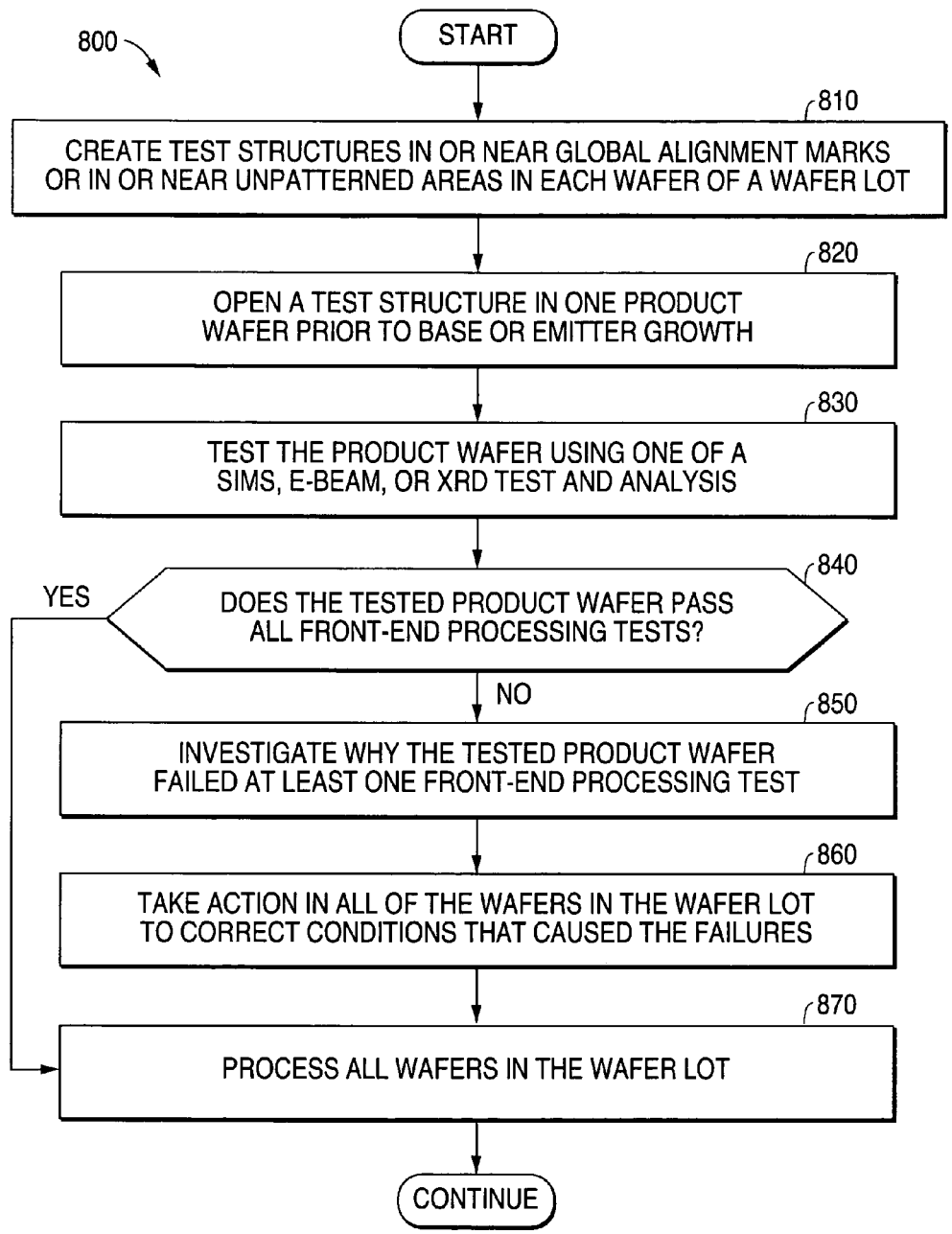
FIG. 8 illustrates a flow chart showing the steps of an advantageous embodiment of the method of the present invention.

FIG. 8 illustrates a flow chart 800 showing the steps of an advantageous embodiment of the method of the present invention. In the first step of the method test structures are created in or near global alignment marks or in or near unpatterned areas in each wafer of a wafer lot (step 810). Then a test structure is opened in one product wafer prior to base or emitter growth (step 820). Then the product wafer is tested using one of: a SIMS test and analysis, an E-beam test and analysis, and an XRD test and analysis (step 830).

Then a determination is made whether the tested product wafer passed all front-end processing tests (decision step 840). If the tested product wafer passed all of the front-end processing tests, then all of the wafers in the wafer lot are processed (step 870). If the tested product wafer did not pass all of the front-end processing tests, then an investigation is carried out to determine why the tested product wafer failed at least one front-end processing test (step 850). Then action is taken in all of the wafers of the wafer lot to correct the condition that caused the failure (step 860). If the condition cannot be corrected, then the wafers in the wafer lot are discarded. If the condition is corrected, then all of the corrected wafers in the wafer lot are processed (step 870).

The system and method of the present invention makes it possible to obtain wafer level information about the front-end processing of the wafers. The system and method of the present invention also provides the opportunity to use SIMS/E-Beam/XRD testing to closely monitor the Germanium (Ge) content and the dopant content of the wafers, and the thickness variations of the wafers, and the defect density of the wafers.

Utilizing the test areas of the present invention eliminates the need to build individual test structures within product dies and eliminates the need to build scribe line structures near the product dies. Utilizing the test areas of the present invention also eliminates the risk of damaging the product dies from possible electrostatic discharges due to exposures from ion beams, electron beams, or X-ray beams.

Although the present invention has been described with an exemplary embodiment, various changes and modifications may be suggested to one skilled in the art. It is intended that the present invention encompass such changes and modifications as fall within the scope of the appended claims.

What is claimed is:

1. A method of testing a semiconductor wafer, said method comprising the steps of:
   manufacturing a test structure in a non-yield area of said semiconductor wafer; and
   performing a test on said test structure using one of: a secondary ion mass spectroscopy test, an electron beam test, and an X-ray diffraction test.

2. The method as set forth in claim 1 wherein said non-yield area comprises an area within a global alignment mark of said semiconductor wafer.

3. The method as set forth in claim 2 wherein said area within said global alignment mark comprises an unpatterned area within said global alignment mark.

4. The method as set forth in claim 1 wherein said non-yield area comprises an area near a global alignment mark of said semiconductor wafer.

5. The method as set forth in claim 1 wherein said non-yield area comprises an area within an unpatterned area of said semiconductor wafer.

6. The method as set forth in claim 1 wherein said non-yield area comprises an area near an unpatterned area of said semiconductor wafer.

7. The method as set forth in claim 1 wherein said test structure has an area that is at least one hundred microns square.

8. A method of testing a semiconductor wafer, said method comprising the steps of:
   manufacturing a test structure within a non-yield area of said semiconductor wafer;
   opening said test structure;
   processing said semiconductor wafer; and
   performing a test on said test structure using one of: a secondary ion mass spectroscopy test, an electron beam test, and an X-ray diffraction test.

9. The method as set forth in claim 8 wherein said test structure is located within a global alignment mark of said semiconductor wafer.

10. The method as set forth in claim 9 wherein said global alignment mark comprises a global clear box image of said semiconductor wafer.

11. The method as set forth in claim 10 wherein said test structure is located with an unpatterned area of said global clear box image.

12. The method as set forth in claim 8 wherein said non-yield area comprises an unpatterned area of said semiconductor wafer.

13. A method of testing a plurality of semiconductor wafers in a semiconductor wafer lot, said method comprising the steps of:
manufacturing a test structure within a non-yield area of each of said plurality of semiconductor wafers;
opening a test structure in at least one semiconductor wafer;
processing said at least one semiconductor wafer; and
performing a test on said test structure in said at least one semiconductor wafer using one of: a secondary ion mass spectroscopy test, an electron beam test, and an X-ray diffraction test.

14. The method as set forth in claim 13 further comprising the steps of:
determining whether said tested semiconductor wafer has passed a front-end processing test; and
processing all semiconductor wafers in said semiconductor wafer lot if said tested semiconductor wafer has passed said front-end processing test.

15. The method as set forth in claim 13 wherein said non-yield area comprises one of: an unpatterned area of said semiconductor wafer, a global alignment mark of said semiconductor wafer, and an unpatterned area of a global alignment mark of said semiconductor wafer.

16. The method as set forth in claim 13 wherein said test structure has an area that is at least one hundred microns square.

17. A semiconductor wafer comprising:
a test structure located within a non-yield area of said semiconductor wafer,
wherein said test structure is large enough to perform a test that comprises one of: a secondary ion mass spectroscopy test, an electron beam test, and an X-ray diffraction test; and
wherein said non-yield area comprises one of: an unpatterned area of said semiconductor wafer, a global alignment mark of said semiconductor wafer, and an unpatterned area of a global alignment mark of said semiconductor wafer.

18. The semiconductor wafer as set forth in claim 17 wherein said test structure has an area that is at least one hundred microns square.

19. The semiconductor wafer as set forth in claim 17 wherein said non-yield area comprises a global clear box image of said semiconductor wafer.

20. The semiconductor wafer as set forth in claim 17 wherein said test structure is located near one of: an unpatterned area of said semiconductor wafer and a global alignment mark of said semiconductor wafer.

* * * * *